United States Patent
Demmer et al.

(10) Patent No.: US 7,004,177 B2
(45) Date of Patent: Feb. 28, 2006

(54) METHOD AND DEVICE FOR DETECTING FOREIGN BODIES IN CIGARETTES

(75) Inventors: Udo Demmer, Pinnebeg (DE); Volker Hausen, Hamburg (DE)

(73) Assignee: Reemtsma Cigarettenfabriken GmbH, (DE)

( * ) Notice: Subject to any disclaimer, the term of this patent is extended or adjusted under 35 U.S.C. 154(b) by 341 days.

(21) Appl. No.: 10/343,517

(22) PCT Filed: Jul. 18, 2001

(86) PCT No.: PCT/EP01/08313

§ 371 (c)(1),
(2), (4) Date: May 23, 2003

(87) PCT Pub. No.: WO02/09539

PCT Pub. Date: Feb. 7, 2002

(65) Prior Publication Data

US 2003/0178036 A1   Sep. 25, 2003

(30) Foreign Application Priority Data

Jul. 31, 2000   (DE) ................................ 100 37 180

(51) Int. Cl.
*A24B 15/22*  (2006.01)

(52) U.S. Cl. ...................... 131/299; 131/290; 131/905; 131/908

(58) Field of Classification Search ................ 131/290, 131/299, 905, 908
See application file for complete search history.

(56) References Cited

U.S. PATENT DOCUMENTS

| 4,707,652 A | 11/1987 | Lowitz |
| 5,476,108 A | 12/1995 | Dominguez |
| 5,736,864 A | 4/1998 | Moller |

FOREIGN PATENT DOCUMENTS

| DE | 3905658 | 8/1990 |
| DE | 19705260 | 8/1997 |
| DE | 29719600 U1 | 2/1998 |
| EP | 0902277 | 3/1999 |
| EP | 0889321 | 7/1999 |

*Primary Examiner*—Steven P. Griffin
*Assistant Examiner*—Carmen Lyles-Irving
(74) *Attorney, Agent, or Firm*—Hovey Williams LLP

(57) ABSTRACT

The invention relates to a method for detecting and selecting foreign parts in cigarettes, in which the tobacco is exposed in the vicinity of the cigarette maker to microwave radiation and both a signal $S_D$ relating to the tobacco density and a signal $S_F$ relating to the tobacco moisture are generated. The density signal $S_D$ and moisture signal $S_F$ are evaluated in combination with one another for the detection of the presence or absence of foreign parts in the tobacco.

3 Claims, 14 Drawing Sheets

METHOD AND DEVICE FOR DETECTING FOREIGN BODIES IN CIGARETTES

BACKGROUND OF INVENTION

1. Field of the Invention

The invention relates to a method for detecting and selecting foreign parts in cigarettes, in which the tobacco is exposed to microwave radiation in the area of the cigarette maker (i.e. a cigarette making machine) and both a signal $S_D$ relating to the tobacco density and a signal $S_F$ relating to the tobacco moisture are generated.

2. Discussion of Prior Art

From German DE 197 05 260 A1 both a method and an apparatus are known for detecting at least one characteristic of a substance like the moisture mass and/or dry mass of tobacco by evaluating the unbalanced of microwave resonator which is caused by the presence of the substance, wherein microwaves with two differing frequencies are applied to the resonator and the resonator frequency shift and the dampening are analysed in comparison to the resonance curve which is free of the substance.

The EP 0 889 321 A1 discloses a microwave resonator for measuring the density profile and/or the moisture profile in longitudinal direction of a sample with high precision and local resolution, wherein the resonator is filled with a dielectric and with the cavity having a substantially smaller thickness than the lateral dimensions measured under a dimension orthogonal thereto.

In the tobacco industry it is necessary for the purpose of maintaining product quality to detect and remove foreign parts contained in the raw tobacco. The term foreign part is understood to mean any non-tobacco material.

The U.S. Pat. No. 4,707,652 discloses a method for the detection of foreign parts in cigarette tobacco by the application of electromagnetic stray radiation, which is analysed.

The U.S. Pat. No. 5,476,108 also relates to the detection of foreign parts in cigarette tobacco, the tobacco being examined with near infrared radiation if a foreign part is detected, a signal is generated for an ejector which includes a pressurised air nozzle, said nozzle thereupon directing an air jet against the cigarette containing said foreign part to remove it from the work flow.

Lastly, German DE 297 19 600 U1 discloses an apparatus for detecting inhomogenities and foreign parts in a material layer, wherein the material layer is treated with particle beams or electromagnetic radiation and the transmitted or reflected intensity in analysed.

These methods for the detection and removal of foreign parts in the cigarette maker are only usable to a limited extent and consequently, based on all foreign parts which might occur, have only an inadequate efficiency.

Apart from purely metal detecting devices or air and screen classifying methods, the prior art more particularly uses optical image evaluation methods in the tobacco processing field.

These methods suffer from the following disadvantages:

The effect of such installations is based on the optical detection of foreign parts. Therefore the tobacco mass stream must be thinned into a monolayer, which can only be brought about through high costs on equipment and space.

The detection rates are material-specific and in particular highly dependent on the colour and size of the foreign parts. Small foreign parts having a similar colour to tobacco are virtually undetectable.

Apart from the actual foreign parts methodically always good tobacco material is also discharged. This increases undesired tobacco losses and leads to additional costs.

In order that the detection and removal of foreign parts in conventional mass streams have any prospect of success, the foreign part detection installations for cigarettes are preferably located upstream of the tobacco cutting stage. However, not only is the raw tobacco contaminated with foreign parts, but also during the tobacco processing operation there is a potential risk of foreign parts entering the tobacco. Thus, despite the installed foreign part seeking installations, there is a risk that foreign parts can still enter the cigarette maker.

Admittedly on the cigarette maker there is a functional unit for the separation of coarse parts, such as e.g. small and undesired stem fragments or so-called winnower stems, but this unit is unable to remove foreign parts with an adequate efficiency, so that there is a risk of foreign parts ultimately entering the cigarette.

OBJECTS AND SUMMARY OF THE PRESENT INVENTION

It is therefore an object of the invention to provide a method for detecting foreign parts in a finished tobacco sod, which is usable on the cigarette maker and requires no radioactive radiation and which is improved compared with the known methods. A cigarette rod containing foreign parts is to be detected and, directly following its detectors, automatically ejected from the production process.

To achieve this object the method of the aforementioned type is used and is characterised in that the density signal $S_O$ and moisture signal $S_F$ are evaluated in combined form in order to detect the presence or absence of foreign parts in the tobacco.

Therefore, the present invention offers a solution to the detection of foreign parts directly in the cigarette maker on finished cigarettes and having a high efficiency, whilst obviating the aforementioned disadvantages of foreign part seeking installations in the tobacco processing area.

In the method according to the invention for the detection of foreign parts in cigarettes, the continuous rod formed is exposed prior to the cutting into individual rods and in the area of the cigarette maker to microwave radiation and both a signal $S_O$ relating to the rod density and signal $S_F$ relating to the rod moisture is, generated and then by means of data processing a combination signal $S_K$ is calculated, which is significant and with high sensitivity detects any foreign parts which may be present in the cigarette rod. The term rod moisture is understood to mean the percentage of water in the rod, based on its dry weight.

The present invention is based on the following idea:

For some time it has been possible to determine with a microwave measuring unit the tobacco density of a cigarette rod. The signals of this microwave measuring unit provide a basis for regulating type cigarette weight.

The measuring method is physically based on the evaluation of the dipole relaxation of water molecules in a moist material sample. For this purpose the measurement material is brought into the field of a resonator. When the material to be measured is located in the electromagnetic field of the resonator, the resonant frequency of the resonator is reduced compared with that of the empty resonator, whereas the peak width of the resonance line is greater than that of the empty resonator. The higher the material moisture content, the greater these two effects.

The two parameters determinable by measurement are influenced not only by the material moisture content, but also the packing density of the sample material within the field range of the resonator. Therefore the method is suitable for the simultaneous measurement, independently of one another, of two measured values, namely the material moisture independently of the packing density, if a moisture calibration is performed by means of reference measurements, as well as the material density independently of the material moisture, if a density calibration is performed using reference measurements.

When measuring the density of a tobacco rod by the microwave resonance measurement principle, automatically and virtually as a waste product a measured value for the material moisture is obtained, expressed e.g. as the "percentage water content (% $H_2O$)", which is not further used.

A foreign part present in the tobacco rod is identified in that its density and also its material moisture differs from that of the remaining tobacco rod. Only through the combined evaluation of both signals, i.e. density and moisture, is one in a position to detect with high sensitivity and precision foreign parts and to discharge the cigarette in question in a following stage. If only the density or only the moisture was evaluated, misinterpretations would occur, because the normal tobacco rod without foreign parts is subject to certain random and irregular density and moisture fluctuations.

This principle of foreign part detection in cigarette makers has already been recognised and tested in the laboratory using a commercial microwave measuring device for measuring the tobacco density and moisture. For this purpose measurements were performed on cigarette rods manually doped with non-tobacco parts or particles.

The invention relates further to an apparatus for carrying out said method wherein such portions of a tobacco rod can be removed which contain undesired foreign parts. The apparatus is based on a microwave resonator as disclosed in EP 0 889 321 A1 i.e. one with an upper and lower metallic wall between which ceramic material is sandwiched. A passage extends through metallic plates or walls and through the ceramic material, and the material to be checked is moved through said passage. The signals generated by the microwave resonator are applied to a processing circuit which controls an ejector when certain criteria are met to remove a predetermined part from the tobacco strand. Normally the ejector is mounted on the cigarette maker or cigarette making machine with a distance to the microwave resonator so that the signals between the microwave resonator and the ejector must be timed. However, it is no problem for a skilled man to achieve such timing. For example, it is possible to provide the main shaft of the cigarette maker with an encoder generating signals which are a clear identification of the working speed of the cigarette machine. In one example the encoder is a rotating disk which is rigidly coupled to the main shaft of the cigarette maker so that it always rotates with the same speed as the main shaft of the cigarette maker. Of course it is possible to let the disk rotate with a higher or lower speed than the speed of the main shaft of the cigarette maker. All that is necessary is that the relationship between the two speeds is always maintained constant. If the rotating disk is provided with holes or slits or gaps in regular intervals at its periphery, for example with 360 holes or gaps, a light beam from a light source provided one side of the disk and being directed towards a photo cell on the other side of the disk generates 360 pulses for each complete revolution of the disk when passing through the holes or gaps so that each pulse represents one degree of rotational movement. These electrical pulses are processed within an electronic circuit and are used for control the ejector in a timed relationship relative to the microwave resonator. It is no problem for the skilled man to establish how many pulses will be counted until the ejector must be activated. The number of encoder pulses "n", which is necessary until the removing signal has to be applied to the ejector depends on various factors of the cigarette machine, for example the positioning of the measuring sensor, the size of the cigarette or on design parameters of the filter connecting machine.

The ejector can have various designs, for example it can be a simple pressurised air nozzle which emits a strong air jet when activated by an activating signal (also called "removing signal"), said air jet being directed laterally against the tobacco strand and thus blowing a defined area out of the tobacco strand.

In another embodiment the ejector is mounted to the cigarette maker behind the cutting apparatus at position where the cigarettes are already completed. In this embodiment entire cigarettes will be removed from the production process and may be transferred to a tobacco recovering station.

BRIEF DESCRIPTION OF THE DRAWING FIGURES.

The invention is explained in greater detail hereinafter by the following graphs:

FIG. 1 The curve for the density and moisture of a normal cigarette.

FIG. 2 The curve according to FIG. 1 with a wood part as a foreign part.

FIG. 3 The curve of FIG. 1 with a rigid plastic part as the foreign part.

FIG. 4 The curve of FIG. 1 with a rubber part as the foreign part.

FIG. 5 The curve of FIG. 1 with a glass fragment is the foreign part.

FIG. 6 The curve of FIG. 1 with a metal part as the foreign part

FIG. 7 The curve of FIG. 1 with a stone as the foreign part.

FIG. 8 The data pattern for the combination signal of a normal cigarette.

FIG. 9 The data pattern according to FIG. 8 with a wood part as the foreign part.

FIG. 10 The data pattern of FIG. 8 with a rigid plastic part as the foreign part.

FIG. 11 The data pattern according to FIG. 8 with a rubber part as the foreign part.

FIG. 12 The data pattern of FIG. 8 with a glass fragment as the foreign part.

FIG. 13 The data pattern of FIG. 8 with a metal part as the foreign part.

FIG. 14 The data pattern of FIG. 8 with a stone as the foreign part.

DETAILED DESCRIPTION OF THE PREFERRED EMBODIMENT

FIG. 1 shows the measurement points for the density and moisture of a normal tobacco rod. The measurements were performed at 1 mm intervals and are plotted in superimposed manner. The upper curve shows a moisture distribution for a normal cigarette and which is between 10.0 and 10.5% water. Over the same measurement range the density for a normal cigarette fluctuates between 205 and 255 mg/cm3, the mean value being approximately 220 mg/cm3.

If according to FIG. 2 a wood part was present in the tobacco rod, there would be a change both to the density and the moisture in this area leading to clear peaks in the area of 18 to 28 mm.

FIG. 3 shows the curve path for a rigid plastic part revealing a clear density peak between 12 and 20 mm and a corresponding moisture peak between 12 and 20 mm.

Figure 1:
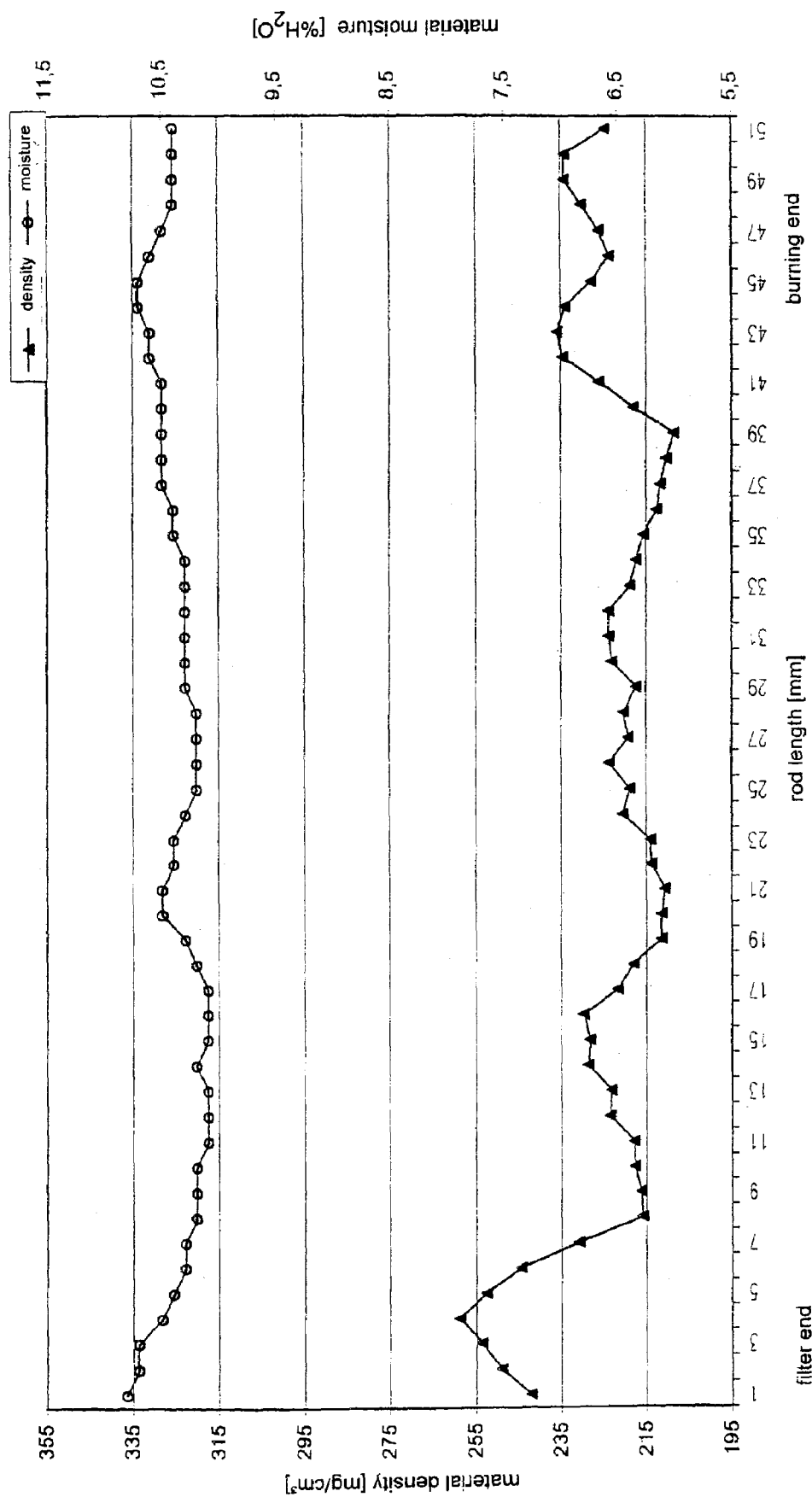
Figure 2:
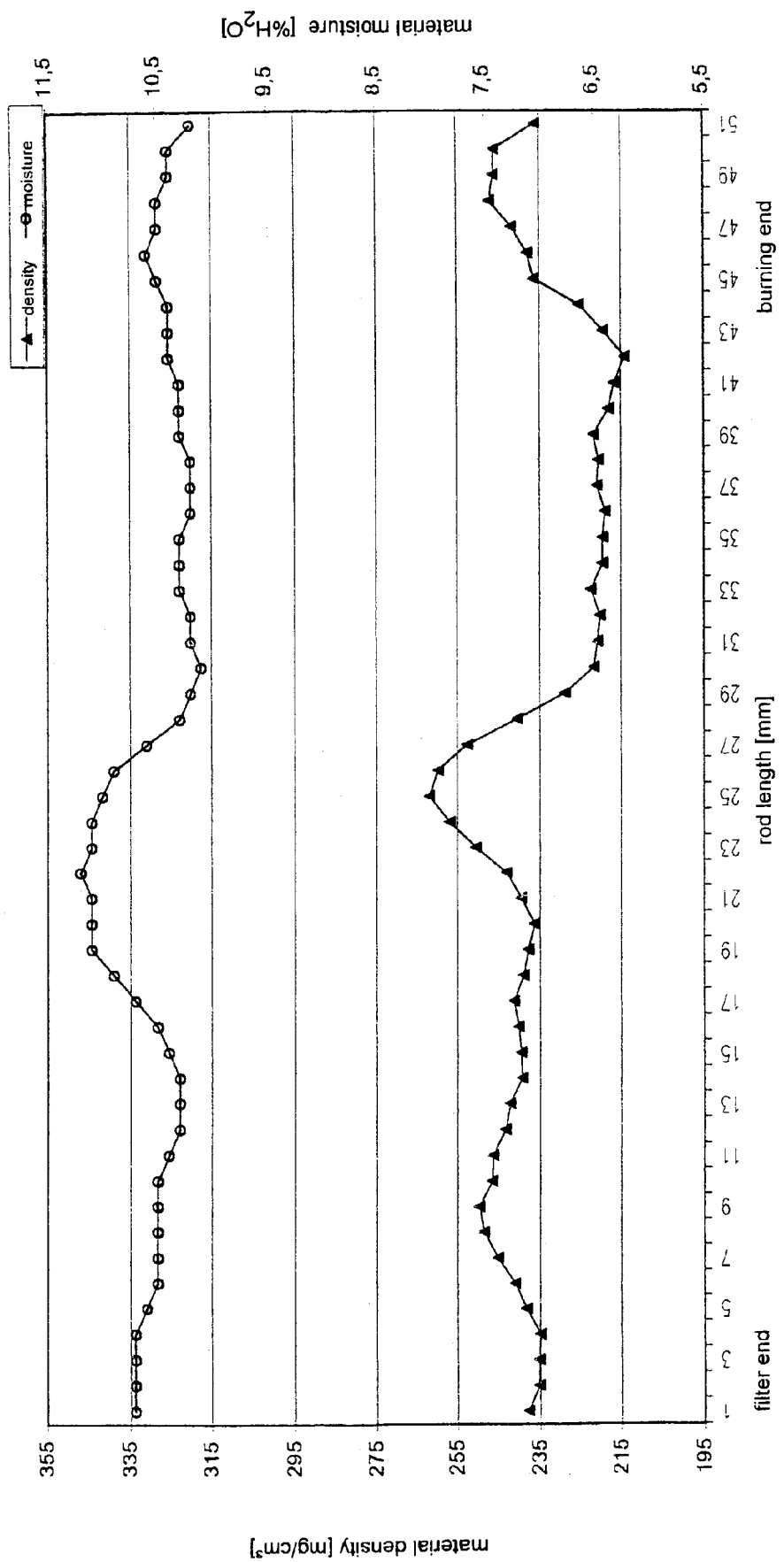
Figure 3:
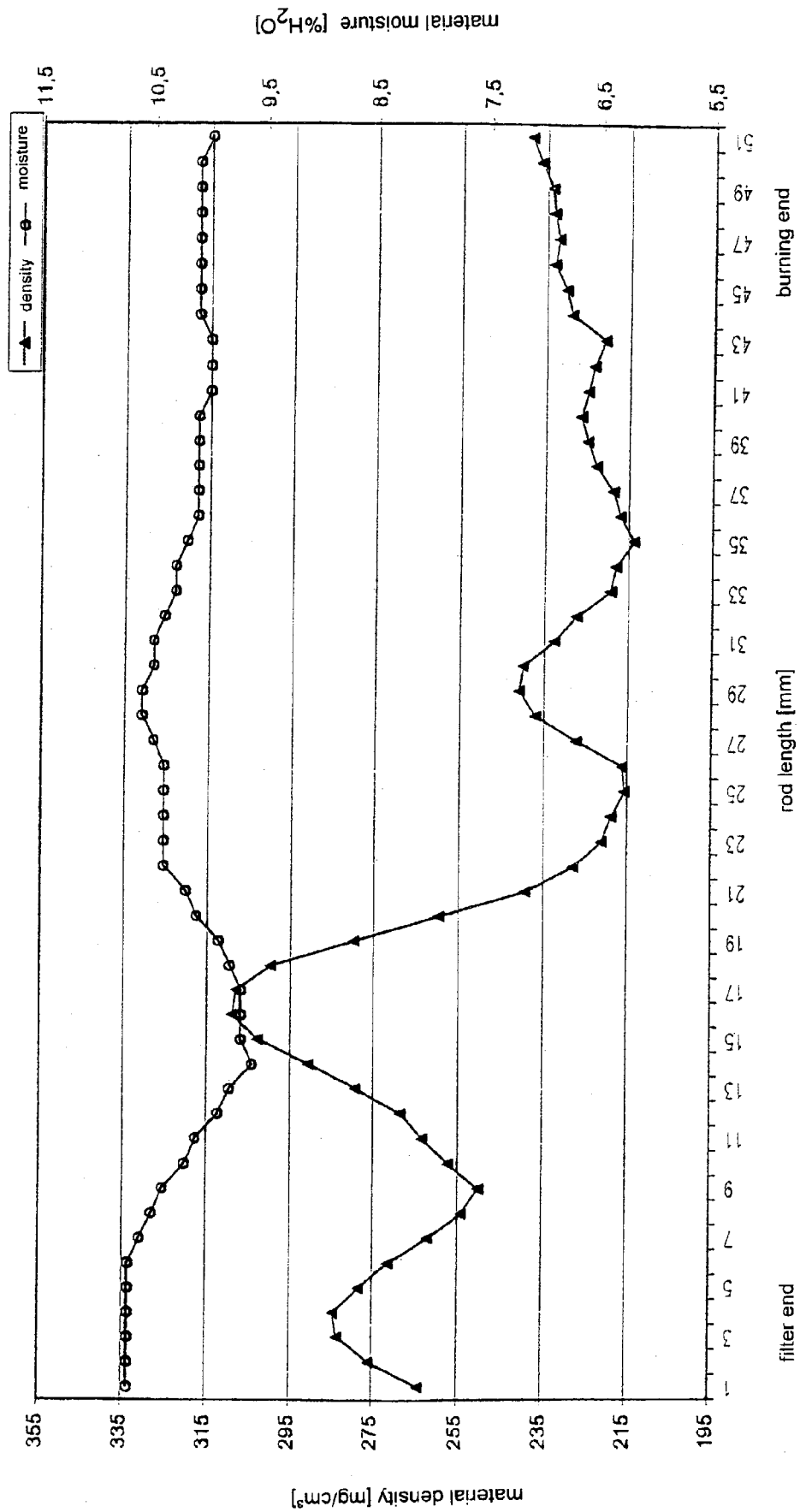
Figure 4:
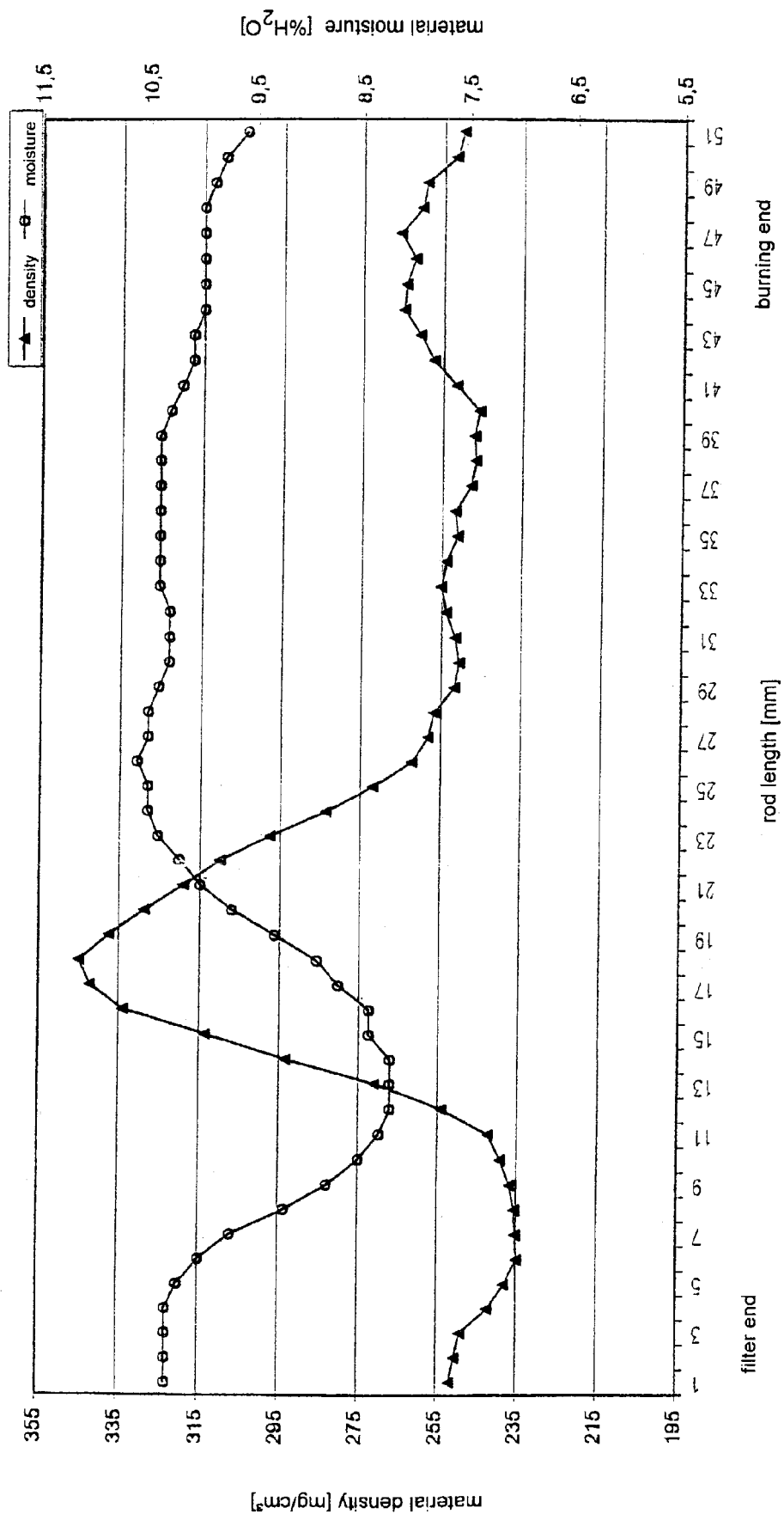
FIG. 4 shows the curve for a rubber part as the foreign part, leading to clear peaks between 8 and 25 mm.
Figure 5:
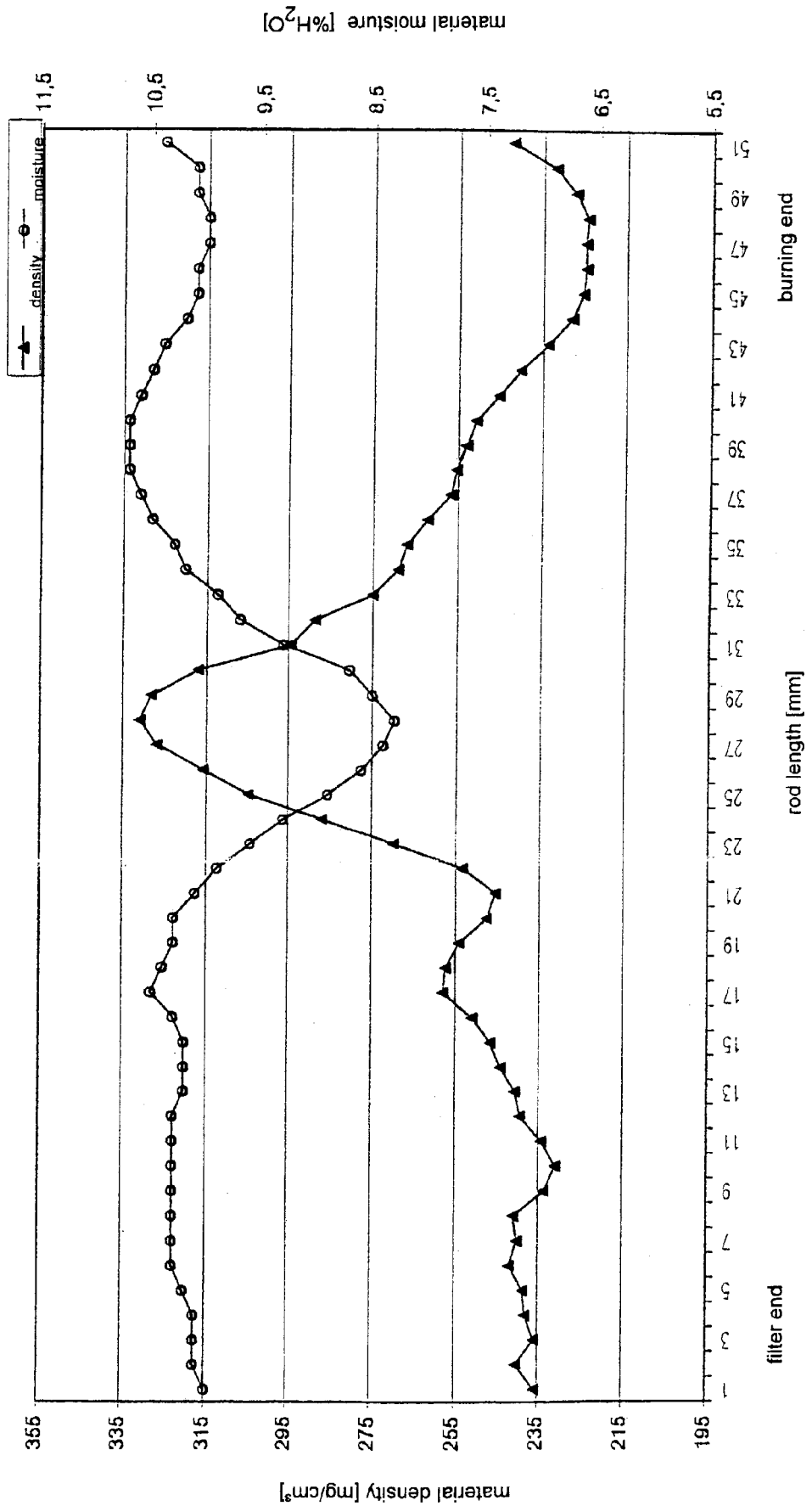
FIG. 5 shows the curve on a tobacco rod with a glass fragment as the foreign body. Both the density and moisture curves reveal clear peaks between 22 and 33 mm enabling the conclusion to be drawn that a foreign part is present.
Figure 6:
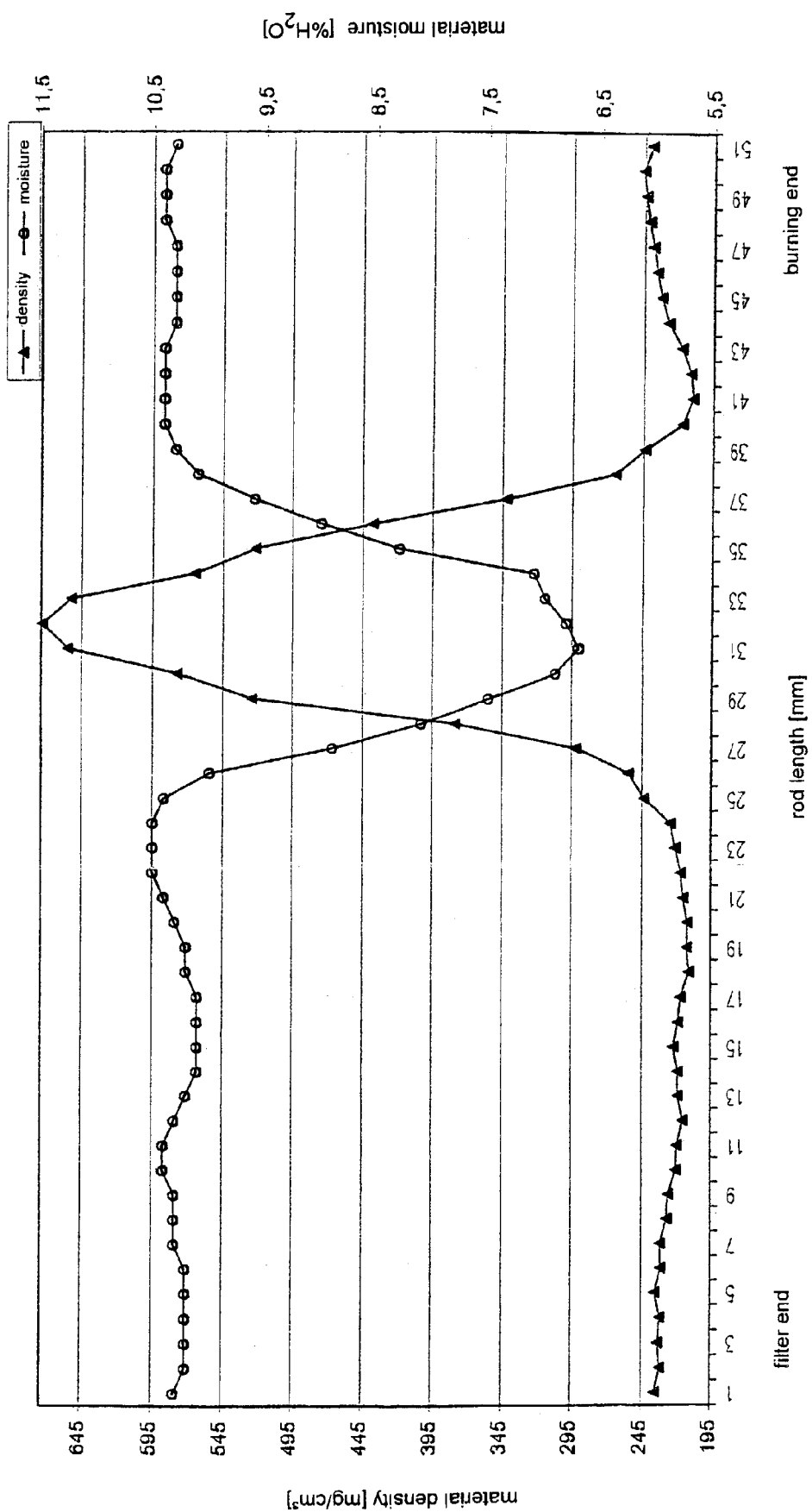
FIG. 6 shows the curve for a metal part as the foreign part with even more pronounced peaks between 27 and 38 mm.
Figure 7:
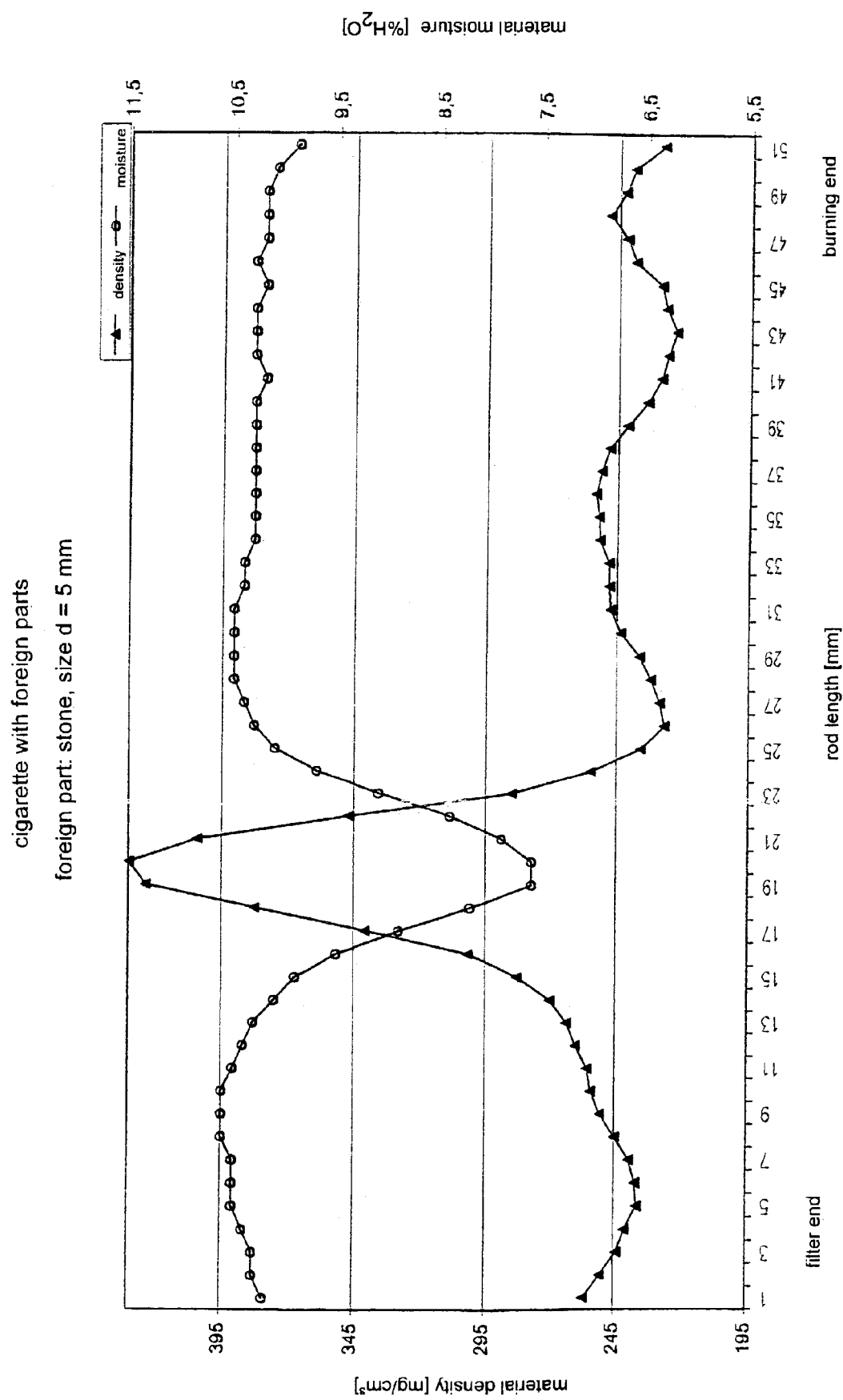

Equally clear peaks result from a stone as the foreign part in the tobacco rod and detected between 15 and 25 mm, as can be clearly gathered from FIG. 7.

From the simultaneous, parallel obtained measured values for the rod density $S_D$ and rod moisture $S_F$, by data processing a combination signal $S_K$ is calculated e.g. in accordance with the following formula:

$$S_K = ABS(\text{mode } x - \text{measured value } x_i)^n_{density} * ABS(\text{mode } x - \text{measured value } x_i)^n_{moisture}$$

The combination signal $S_K$ is the product of the amount of the difference of the mode minus the $i^{th}$ measured value of the density signal and the amount of the $n^{th}$ power of the difference of the mode minus the $i^{th}$ measured value of the moisture signal and identifies in a significant and highly sensitive manner foreign parts in the cigarette rod. The variable n can assume a value between 1 and 5.

The combination signal $S_K$ can also be calculated by using the following formulae:

$$S_K = (\text{mode } x - \text{measured value } x_i)^n_{density} * ABS(\text{mode } x - \text{measured value } x_i)^n_{moisture}$$

or $$S_K = ABS(\text{mode } x - \text{measured value } x_i)^n_{density} * (\text{mode } x - \text{measured value } x_i)^n_{moisture}$$

or $$S_K = (\text{mode } x - \text{measured value } x_i)^n_{density} * (\text{mode } x - \text{measured value } x_i)^n_{moisture}$$

The combination signal $S_K$ is further illustrated hereinafter with the aid of graphs, for which the basis are the primary obtained measured signals according to FIGS. 1 to 7.

Figure 8:
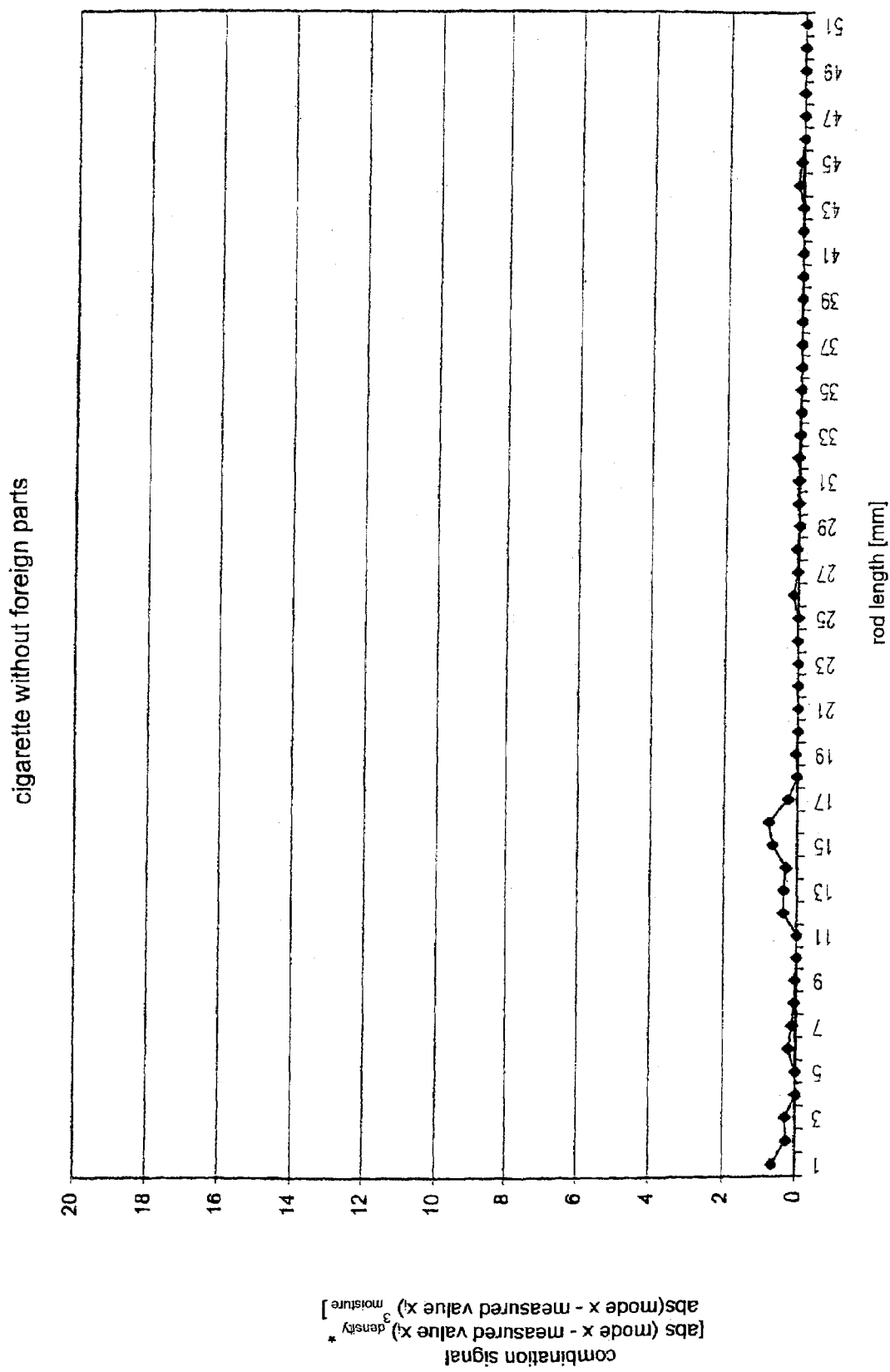

FIG. 8 shows the data points for the combination signal of a normal tobacco rod with intensities varying from the zero line to a maximum value of 1.

Figure 9:
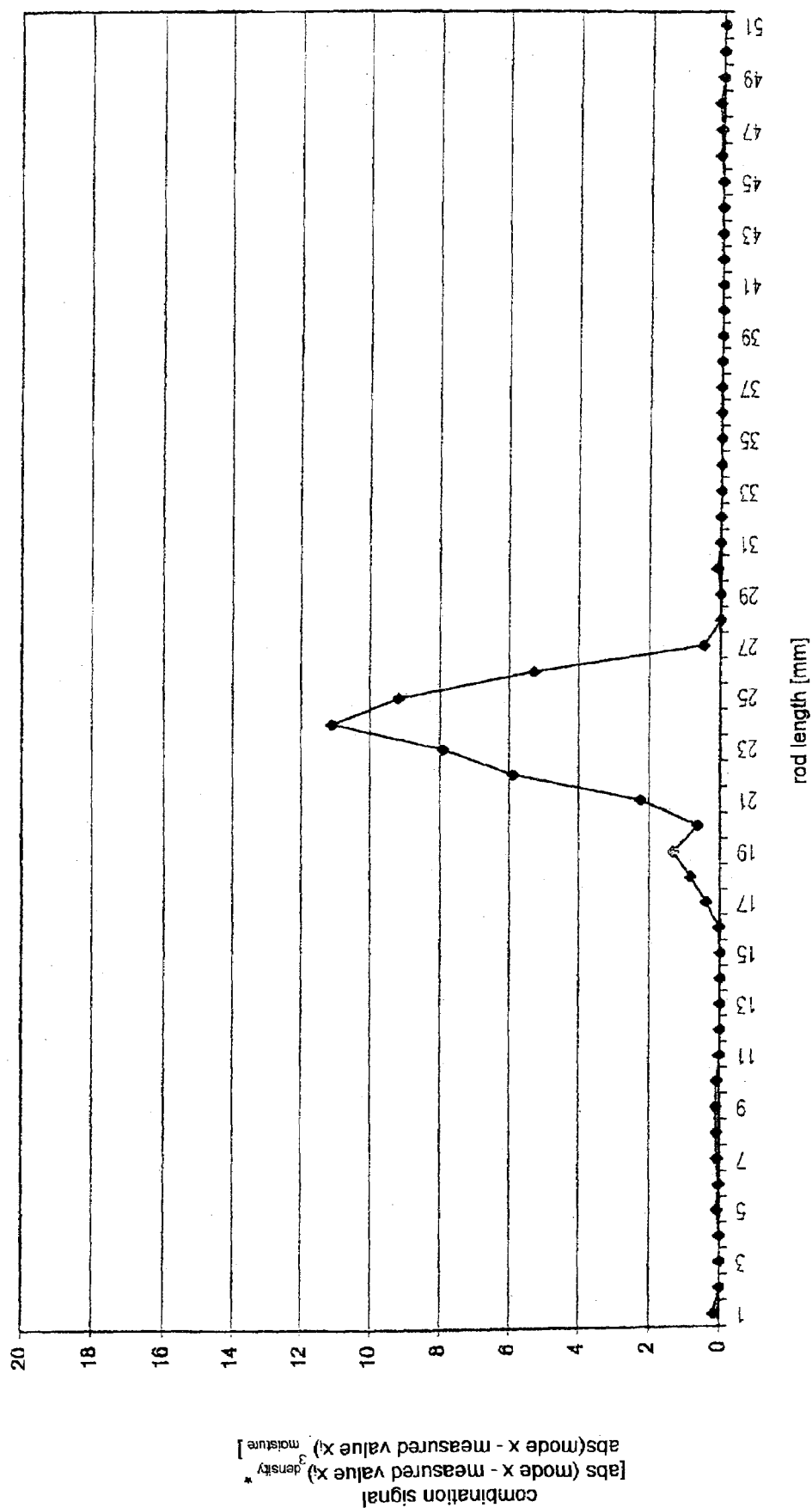

If in accordance with FIG. 9 there was a wood part in the tobacco rod, then between 22 and 26 mm there would a significant peak up to a maximum intensity of the value 11.

Figure 10:
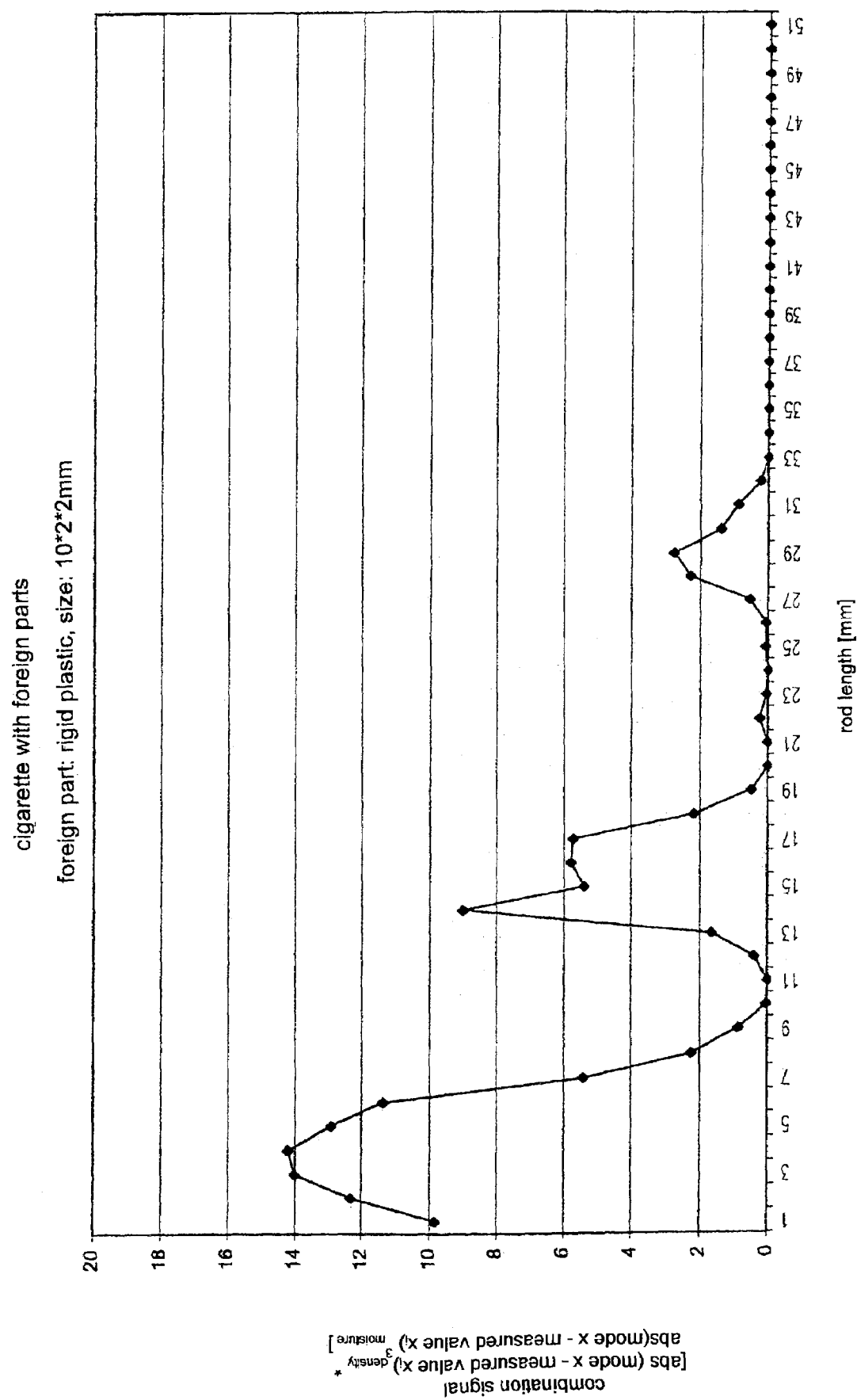

FIG. 10 shows the data pattern for a rigid plastic part revealing a combination signal peak between 14 and 18 mm up to a maximum intensity of value 9.

Figure 11:
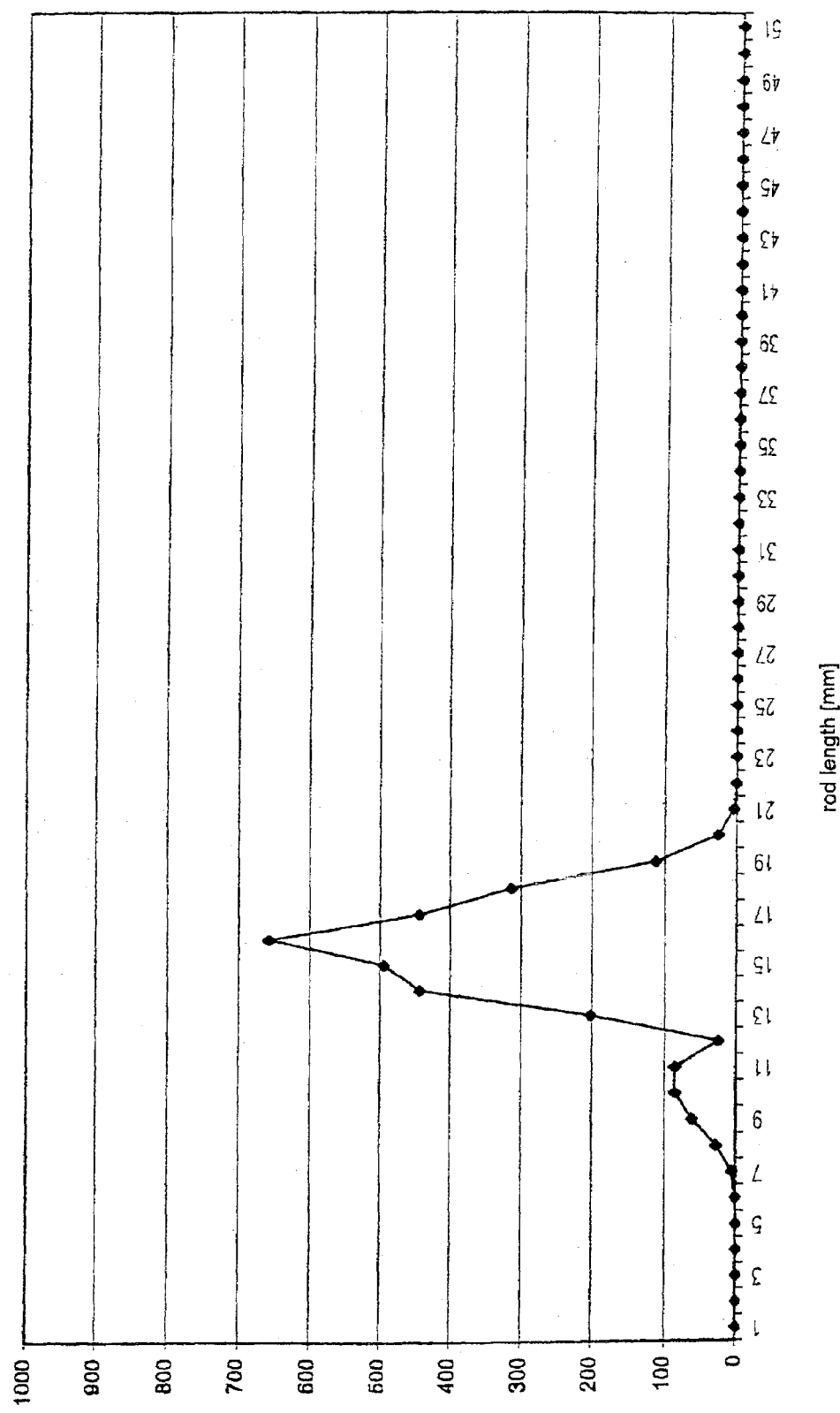

FIG. 11 shows the data pattern for a rubber part as the foreign part, leading to a clear peak between 14 and 18 mm up to e maximum intensity of the value 650.

Figure 12:
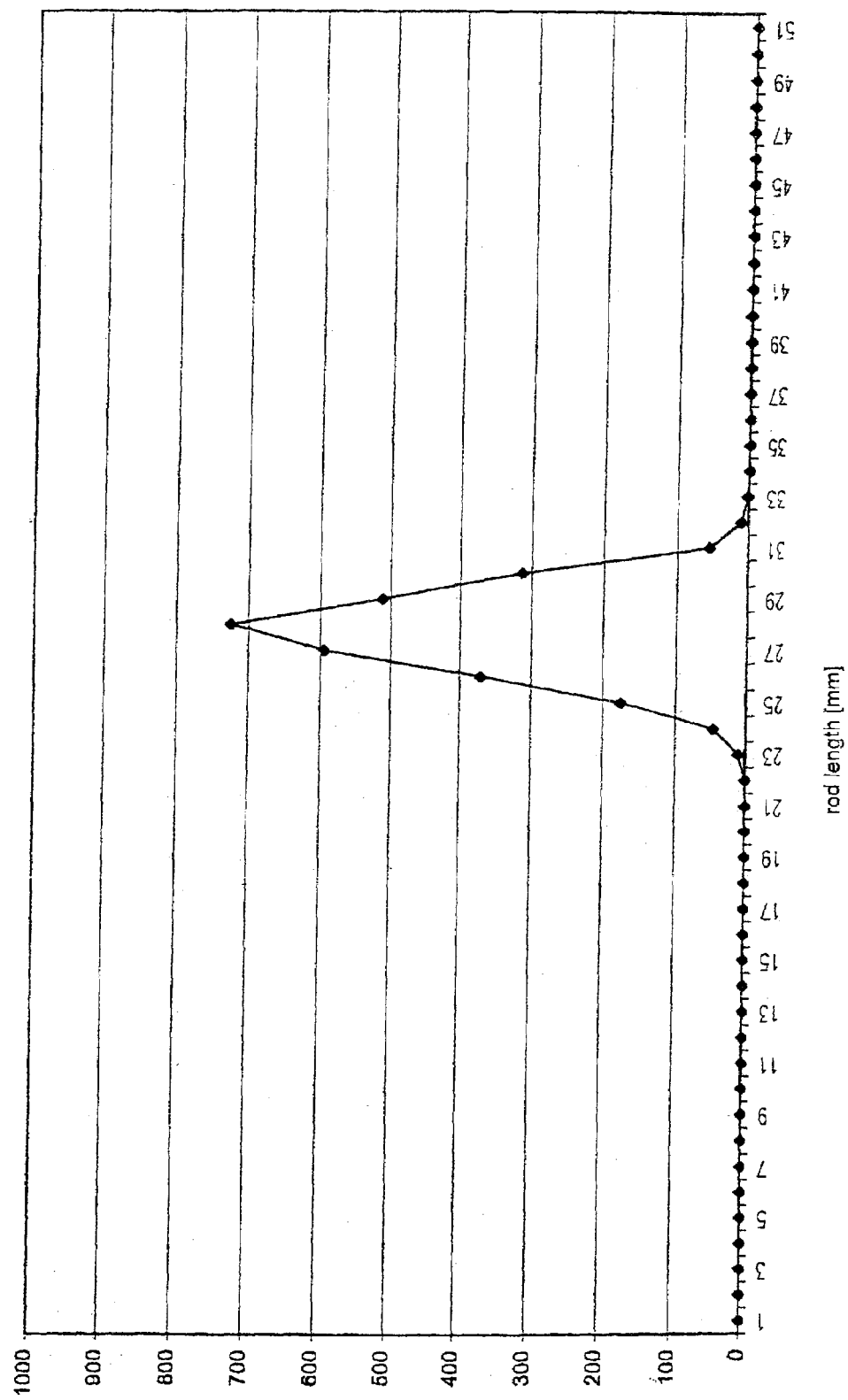

FIG. 12 shows the data pattern on a tobacco rod with a glass fragment as the foreign part. There is a clear peak between 25 and 30 mm up to a maximum intensity of value 700 enabling the conclusion to be drawn that said foreign part is present.

Figure 13:
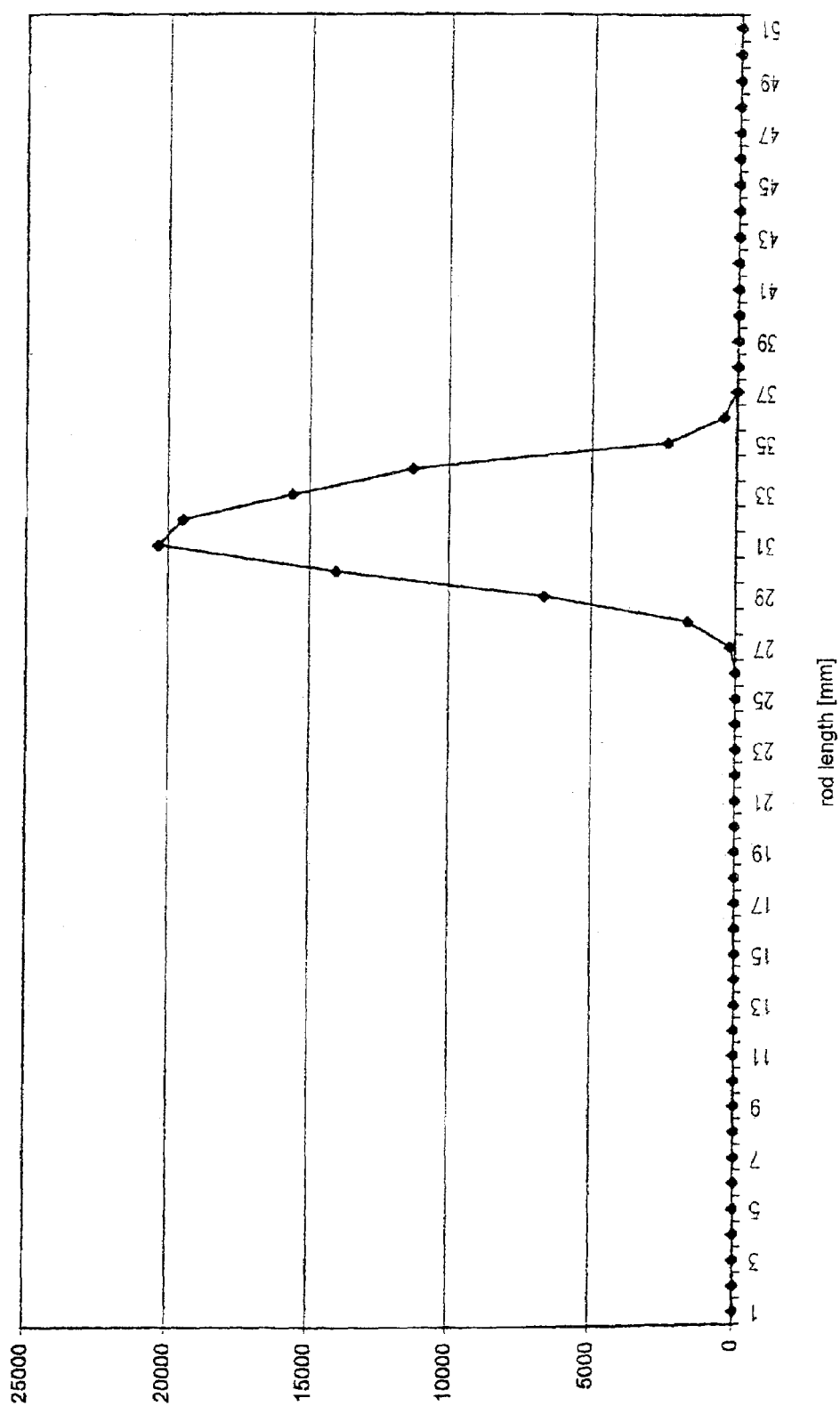

FIG. 13 shows the data pattern for a metal part as the foreign part with an even clearer peak up to a maximum intensity of the value 20,000 between 29 and 35 mm.

Figure 14:
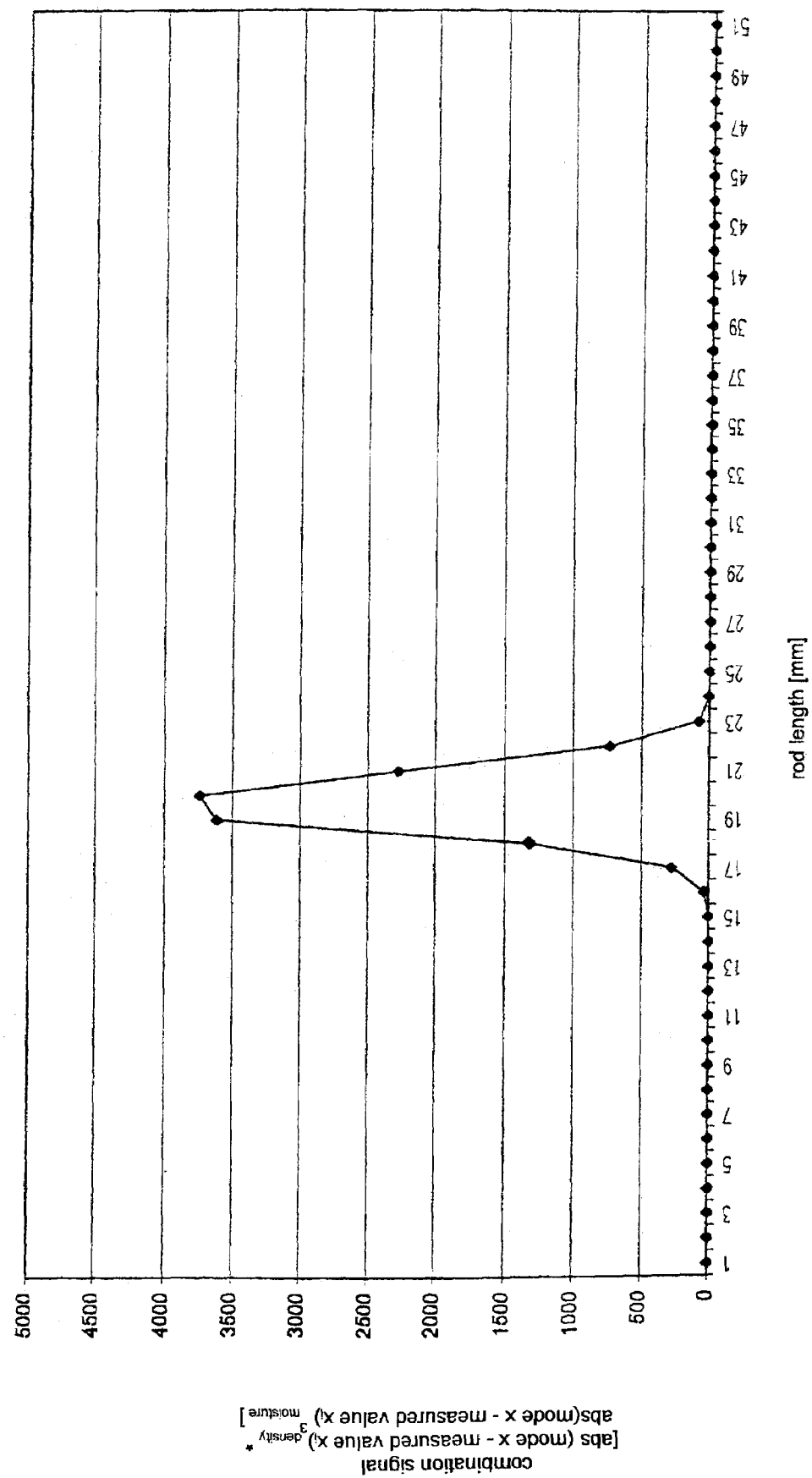

An equally clear peak up to a maximum intensity of value 3,500 is caused by a stone, as the foreign part, in the tobacco rod and detected between 18 and 22 mm, as can be clearly gathered from FIG. 14.

If the combination signal exceeds a threshold to be established, e.g. the value 5, a foreign part signal is generated, which is used for controlling an ejector. This makes it possible to ensure that cigarette rods containing foreign parts are eliminating from the production process and supplied to a separate disposal means.

The invention can equally well be used for rod-like, continuous or portioned bulk material units.

The invention claimed is:

1. A method for detecting and selecting foreign parts in cigarettes, said method comprising the steps of:
    exposing the tobacco in the vicinity of the cigarette maker to microwave radiation;
    generating both a signal $S_D$ relating to the tobacco density and a signal $S_F$ relating to the tobacco moisture using a microwave resonator; and
    evaluating the density signal $S_D$ and moisture signal $S_F$ in combination with one another in order to detect the presence or absence of foreign parts in the tobacco.

2. A method for detecting and selecting foreign parts in cigarettes, said method comprising the steps of:
    exposing the tobacco in the vicinity of the cigarette maker to microwave radiation;
    generating both a signal $S_D$ relating to the tobacco density and a signal $S_F$ relating to the tobacco moisture using a microwave resonator; and
    evaluating the density signal $S_D$ and moisture signal $S_F$ in combination with one another in order to detect the presence or absence of foreign parts in the tobacco,
    further including the step of calculating a combination signal $S_K$ by data processing from the simultaneously obtained measures values for the density signal $S_D$ and moisture signal $S_F$.

3. A method according to claim 2,
    further including the steps of, if the combination signal $S_K$ exceeds an adjustable threshold, generating a foreign part signal and using the foreign part signal to control an ejector for ejecting foreign parts.

* * * * *